US010722408B2

(12) United States Patent
Morimoto

(10) Patent No.: US 10,722,408 B2
(45) Date of Patent: Jul. 28, 2020

(54) WEARABLE ARTICLE HAVING GRAPHICS

(71) Applicant: The Procter & Gamble Company, Cincinnati, OH (US)

(72) Inventor: Koichi Morimoto, Beijing (CN)

(73) Assignee: The Procter & Gamble Company, Cincinnati, OH (US)

(*) Notice: Subject to any disclaimer, the term of this patent is extended or adjusted under 35 U.S.C. 154(b) by 427 days.

(21) Appl. No.: 15/479,672

(22) Filed: Apr. 5, 2017

(65) Prior Publication Data
US 2018/0289565 A1    Oct. 11, 2018

Related U.S. Application Data

(63) Continuation of application No. PCT/CN2017/074259, filed on Feb. 21, 2017, which
(Continued)

(51) Int. Cl.
A61F 13/15    (2006.01)
A61F 13/84    (2006.01)
(Continued)

(52) U.S. Cl.
CPC ............ *A61F 13/84* (2013.01); *A61F 13/496* (2013.01); *A61F 13/49011* (2013.01); *A61F 2013/8497* (2013.01)

(58) Field of Classification Search
CPC .. A61F 13/84; A61F 13/49011; A61F 13/496; A61F 2013/8497
See application file for complete search history.

(56) References Cited

U.S. PATENT DOCUMENTS 2,462,195 A    2/1949    Jacobson
2,513,039 A    6/1950    Miller
(Continued)

FOREIGN PATENT DOCUMENTS

CN    2167695    8/1994
CN    1246324    8/2000
(Continued)

OTHER PUBLICATIONS

International Search Report and Written Opinion, PCT/CN2017/074259.
(Continued)

*Primary Examiner* — Jacqueline F Stephens
(74) *Attorney, Agent, or Firm* — Richard L. Alexander

(57) ABSTRACT

The present disclosure is related to a wearable article continuous in a longitudinal direction and a transverse direction comprising a main body comprising an outer cover layer at the most garment-facing side and a backsheet attached to the skin-facing surface of the outer cover layer, wherein the main body has a front waist panel, a back waist panel and a crotch panel between the front waist panel and the back waist panel, and wherein the longitudinal length of the outer cover layer is longer than the longitudinal length of the crotch panel and shorter than the longitudinal length of the backsheet; a ring-like belt comprising a front belt and a back belt, wherein each of the front belt and the back belt comprises an inner sheet, an outer sheet and a plurality of elastic strands sandwiched therebetween; a front waist graphic region disposed on the front waist panel where the outer cover layer is absent, and a back waist graphic region disposed on the back waist panel where the outer cover layer is absent, wherein at least one of the front waist graphic region and the back waist graphic region comprises a waist graphic printed on the main body; a transitional region
(Continued)

disposed on the front waist panel and the back waist panel where the outer cover layer exists; and a first belt graphic disposed on one or both of the front and back belts, the first belt graphic not being provided by the main body.

20 Claims, 5 Drawing Sheets

Related U.S. Application Data is a continuation-in-part of application No. PCT/CN2016/078774, filed on Apr. 8, 2016.

(51) Int. Cl.
*A61F 13/49* (2006.01)
*A61F 13/496* (2006.01)

(56) References Cited

U.S. PATENT DOCUMENTS

| | | |
|---|---|---|
| 2,632,177 A | 3/1953 | Bigger |
| 3,080,869 A | 3/1963 | Alberts |
| 3,824,812 A | 7/1974 | Matthews et al. |
| D281,540 S | 12/1985 | Ternstrom |
| 5,769,838 A | 6/1998 | Buell et al. |
| 5,787,512 A | 8/1998 | Knox |
| 7,520,873 B2 | 4/2009 | Sosalla et al. |
| 7,896,858 B2 | 3/2011 | Trennepohl et al. |
| 7,901,393 B2 | 3/2011 | Matsuda et al. |
| 8,518,008 B2 | 8/2013 | Toshiyasu et al. |
| 8,555,419 B2 | 10/2013 | Demarest et al. |
| 8,647,319 B2 | 2/2014 | Een et al. |
| 9,023,006 B2 | 5/2015 | Shunsuke et al. |
| 9,233,031 B2 | 1/2016 | Ichihara et al. |
| 9,358,162 B2 | 6/2016 | Kuwano et al. |
| 9,827,149 B2 | 11/2017 | LaVon et al. |
| 10,064,763 B2 | 9/2018 | Takahashi et al. |
| 2004/0243083 A1 | 12/2004 | Matsuda et al. |
| 2005/0107763 A1 | 5/2005 | Matsuda et al. |
| 2007/0208317 A1 | 9/2007 | Krautkramer et al. |
| 2008/0132872 A1 | 6/2008 | Trennepohl et al. |
| 2011/0251576 A1 | 10/2011 | Ando et al. |
| 2012/0226254 A1 | 9/2012 | Takino |
| 2013/0079742 A1 | 3/2013 | Kuwano et al. |
| 2013/0211363 A1 | 8/2013 | LaVon et al. |
| 2013/0310795 A1 | 11/2013 | Glahn et al. |
| 2013/0310798 A1 | 11/2013 | Glahn et al. |
| 2014/0228798 A1 | 8/2014 | Ashton et al. |
| 2014/0358110 A1 | 12/2014 | Takahashi et al. |

FOREIGN PATENT DOCUMENTS

| | | |
|---|---|---|
| EP | 2659870 | 11/2013 |
| JP | H0871107 | 3/1996 |
| JP | H9271488 | 10/1997 |
| JP | 2001212176 | 8/2001 |
| JP | 2007029479 | 2/2007 |
| JP | 2009125087 | 6/2009 |
| JP | 2012095937 | 5/2012 |
| JP | 2012135519 | 7/2012 |
| JP | 5566550 | 8/2014 |
| JP | 2014150909 | 8/2014 |

OTHER PUBLICATIONS

International Search Report and Written Opinion, PCT/CN2016/078774.

All Office Actions, U.S. Appl. No. 15/479,604, ee Pair (P&G AA1070M).

All Office Actions, U.S. Appl. No. 15/479,717, see Pair (P&G AA1072M).

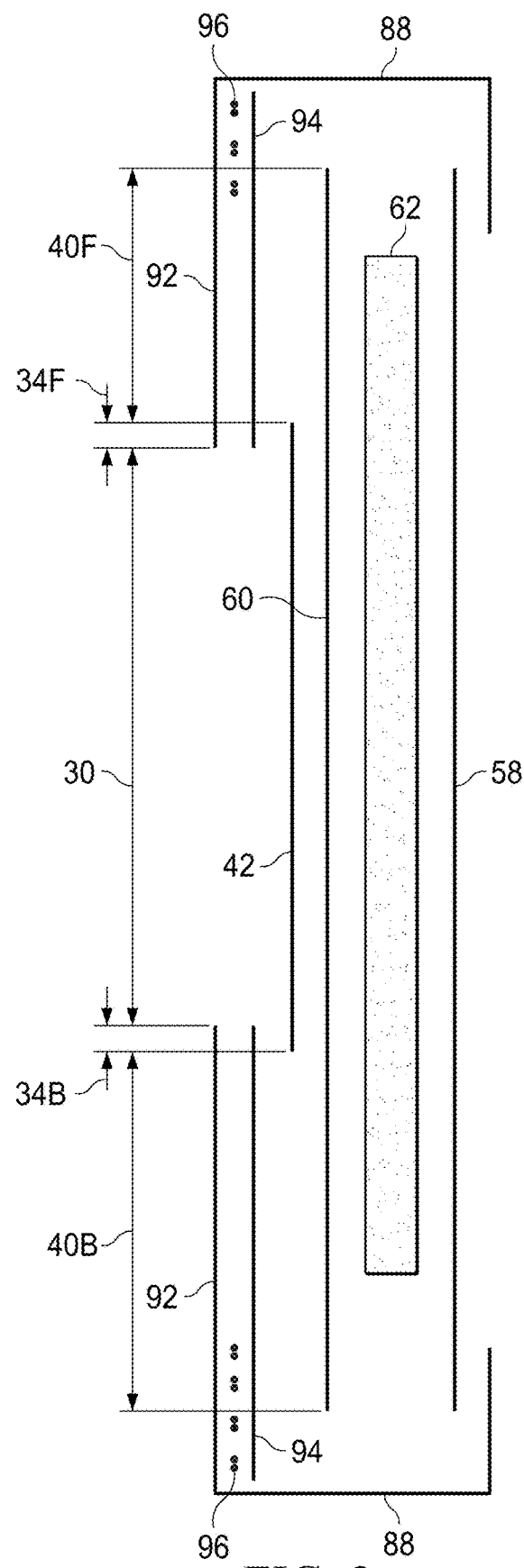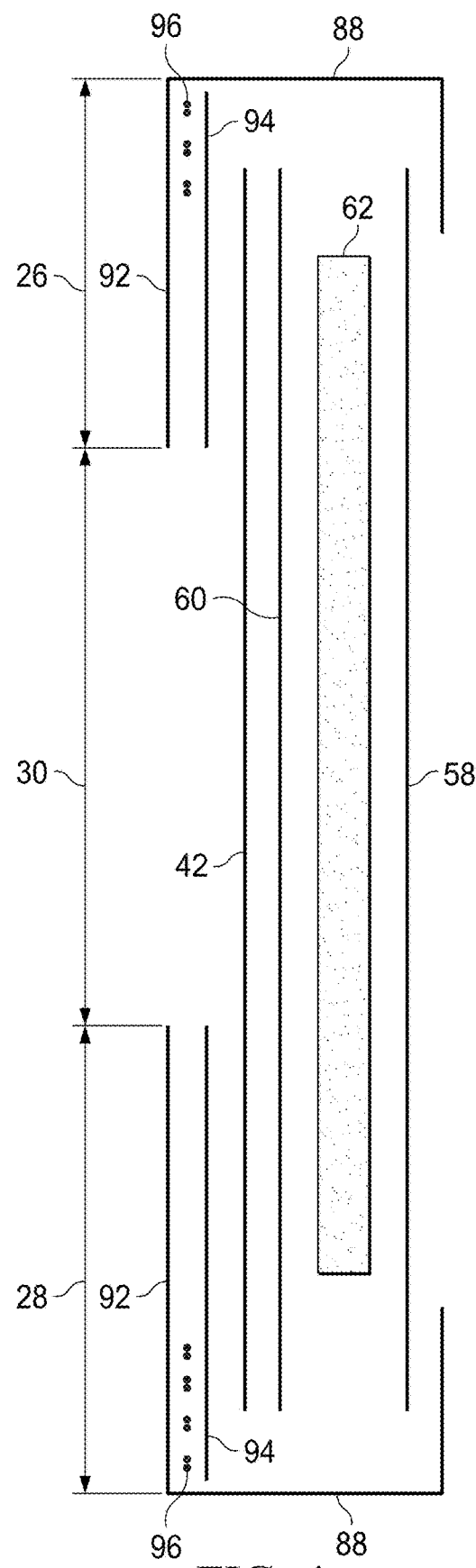
FIG. 3
FIG. 4

WEARABLE ARTICLE HAVING GRAPHICS

CROSS REFERENCE TO RELATED APPLICATIONS

This application claims priority to Application No. CN2017/074259, filed on Feb. 21, 2017, and to Application No. CN2016/078774, filed on Apr. 8, 2016, each of which are herein incorporated by reference in their entirety.

FIELD OF THE INVENTION

The present disclosure relates to wearable articles having graphics in at least one of a front region and a back region.

BACKGROUND OF THE INVENTION

Infants and other incontinent individuals wear wearable articles such as diapers to receive and contain urine and other body exudates. Pull-on wearable articles, or pant-type wearable articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult.

Many pant-type wearable articles use elastic elements secured in an elastically contractible condition in the waist and/or leg openings. Typically, in order to insure full elastic fit about the leg and the waist such as is provided with durable undergarments, the leg openings and waist opening are encircled at least in part with elasticized elements positioned along the periphery of the respective opening.

Pant-type wearable articles having a main body to cover the crotch region of the wearer and a separate elastic belt defining the waist opening and leg opening are known in the art, such as described in PCT Publication WO 2006/17718A. Such pant-type wearable articles may be referred to as belt-type pants. On the other hand, certain pant-type wearable articles are configured such that the outer cover of the wearable main body completely covers the entirety of the garment-facing surface of the article. Such pant-type wearable articles may be referred to as uni-body pants. Belt-type pants, compared to uni-body pants, may be advantageous in that they may have better breathability by having less layers of material in certain areas of the articles, and that they may be manufactured economically. On the other hand, due to the structural difference between the main body and elastic belt, belt-type pants may be disadvantageous in providing printed artwork that provides a visual integrity.

Whether the belt-type or the uni-body type, there is a desire to provide coordinated and integrated graphics on both the main body and the belt of an absorbent article as absorbent articles having such coordinated and integrated graphics can provide more of an underwear-like look and feel, aiding in toilet training. Moreover, the more of an underwear-like look and feel that an absorbent article possesses, the more likely that a user will be willing to accept utilizing the product. Likewise, for wearable articles intended for adults experiencing incontinence, an underwear-like appearance, as opposed to an overall white diaper-like appearance, may have a significant psychological influence on the adult and therefore be important in gaining the adult's acceptance in using the absorbent articles.

In currently available wearable articles, graphics are typically printed only on the main body of the article. The outer layer of the main body, a water impermeable film layer is typically utilized for providing graphics. There are some absorbent articles having printing on the belt. Printing graphics on a nonwoven material consisting of a belt increases production cost significantly as it requires special ink to avoid ink rub-off issue occurred in a user wearing condition.

Based on the foregoing, there is a need for a disposable absorbent article to provide an undergarment-like look and feel. There is also a need for providing such an absorbent article without compromise to the performance as an absorbent article, such as fit, wearability, comfort during wear, prevention of sagging, and prevention of leakage. There is further a need for providing such an absorbent article in an economical manner.

SUMMARY OF THE INVENTION

The present disclosure is directed to a wearable article continuous in a longitudinal direction and a transverse direction comprising a main body comprising an outer cover layer at the most garment-facing side and a backsheet attached to the skin-facing surface of the outer cover layer, wherein the main body has a front waist panel, a back waist panel and a crotch panel between the front waist panel and the back waist panel, and wherein the longitudinal length of the outer cover layer is longer than the longitudinal length of the crotch panel and shorter than the longitudinal length of the backsheet; a ring-like belt comprising a front belt and a back belt, wherein each of the front belt and the back belt comprises an inner sheet, an outer sheet and a plurality of elastic strands sandwiched therebetween; a front waist graphic region disposed on the front waist panel where the outer cover layer is absent, and a back waist graphic region disposed on the back waist panel where the outer cover layer is absent, wherein at least one of the front waist graphic region and the back waist graphic region comprises a waist graphic printed on the main body; a transitional region disposed on the front waist panel and the back waist panel where the outer cover layer exists; and a first belt graphic disposed on one or both of the front and back belts, the first belt graphic not being provided by the main body.

BRIEF DESCRIPTION OF THE DRAWINGS

While the specification concludes with claims particularly pointing out and distinctly claiming the subject matter which is regarded as forming the present disclosure, it is believed that the disclosure will be better understood from the following description which is taken in conjunction with the accompanying drawings and which like designations are used to designate substantially identical elements, and in which:

FIG. 3 is a schematic cross section view of a first embodiment taken along line 4-4 in FIG. 2 of an exemplary wearable article.

FIG. 4 is a schematic cross section view of a wearable article of the prior art.

DETAILED DESCRIPTION OF THE INVENTION

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Graphic" refers to a colored visual presentation. 'Color' or 'colored' as referred to herein includes any primary color except white, i.e., black, red, blue, violet, orange, yellow, green, and indigo as well as any declination thereof or mixture thereof "Non-color' or 'non-colored' refers to the color white which is further defined as those colors having an L* value of at least 94, an a* value equal to 0±2, and a b* value equal to 0±2.

"Disposed" refers to an element being located in a particular place or position

"Joined" refers to configurations whereby an element is directly secured to another element by affixing the element directly to the other element and to configurations whereby an element is indirectly secured to another element by affixing the element to intermediate member(s) which in turn are affixed to the other element.

"Web" refers to a material which is a collection of fibrous elements such as a woven, nonwoven, film, or combination or laminate of any of the foregoing materials.

Wearable Articles

Figure 1:
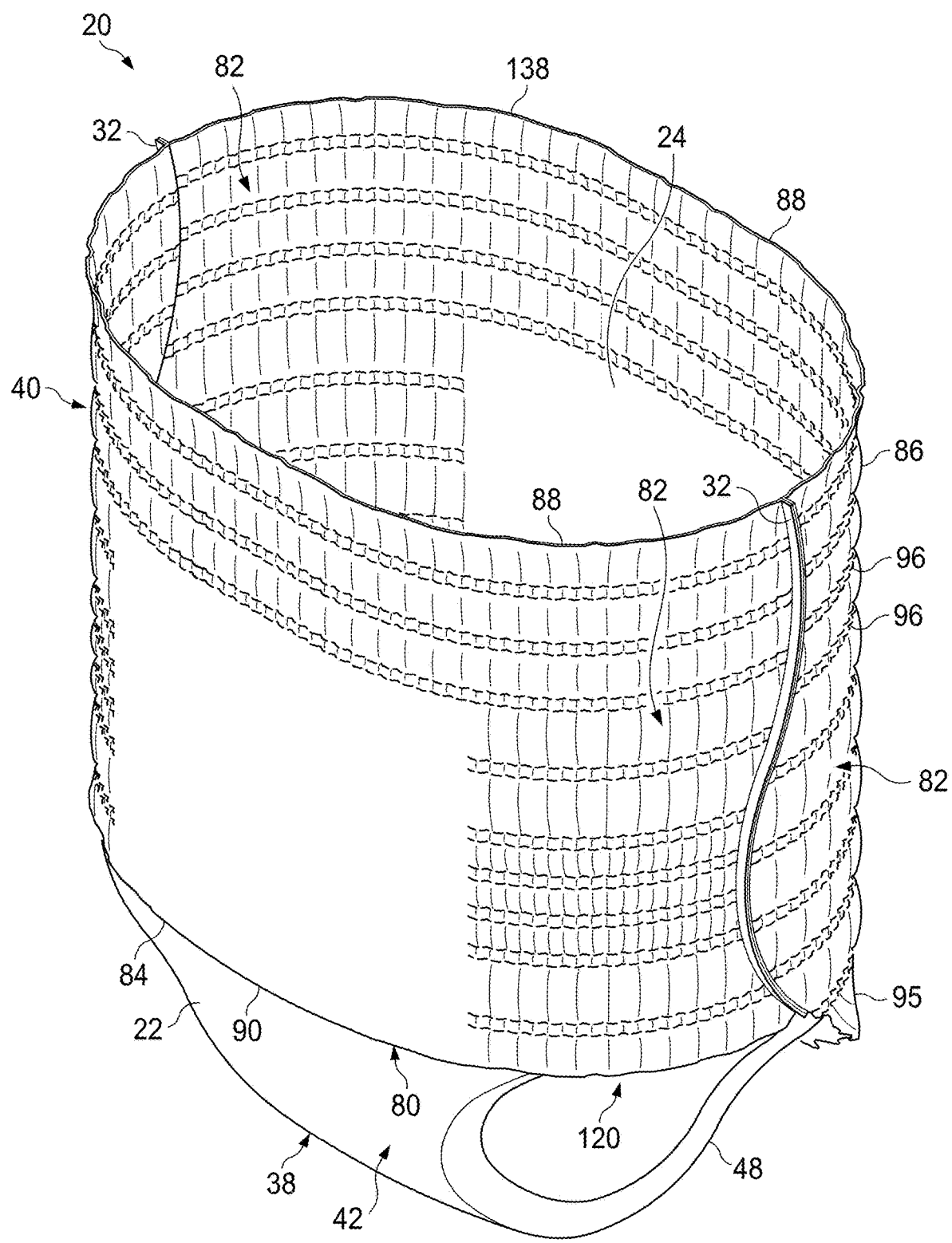
FIG. 1 is a perspective view of one embodiment of a wearable article of the present disclosure.
Figure 2:
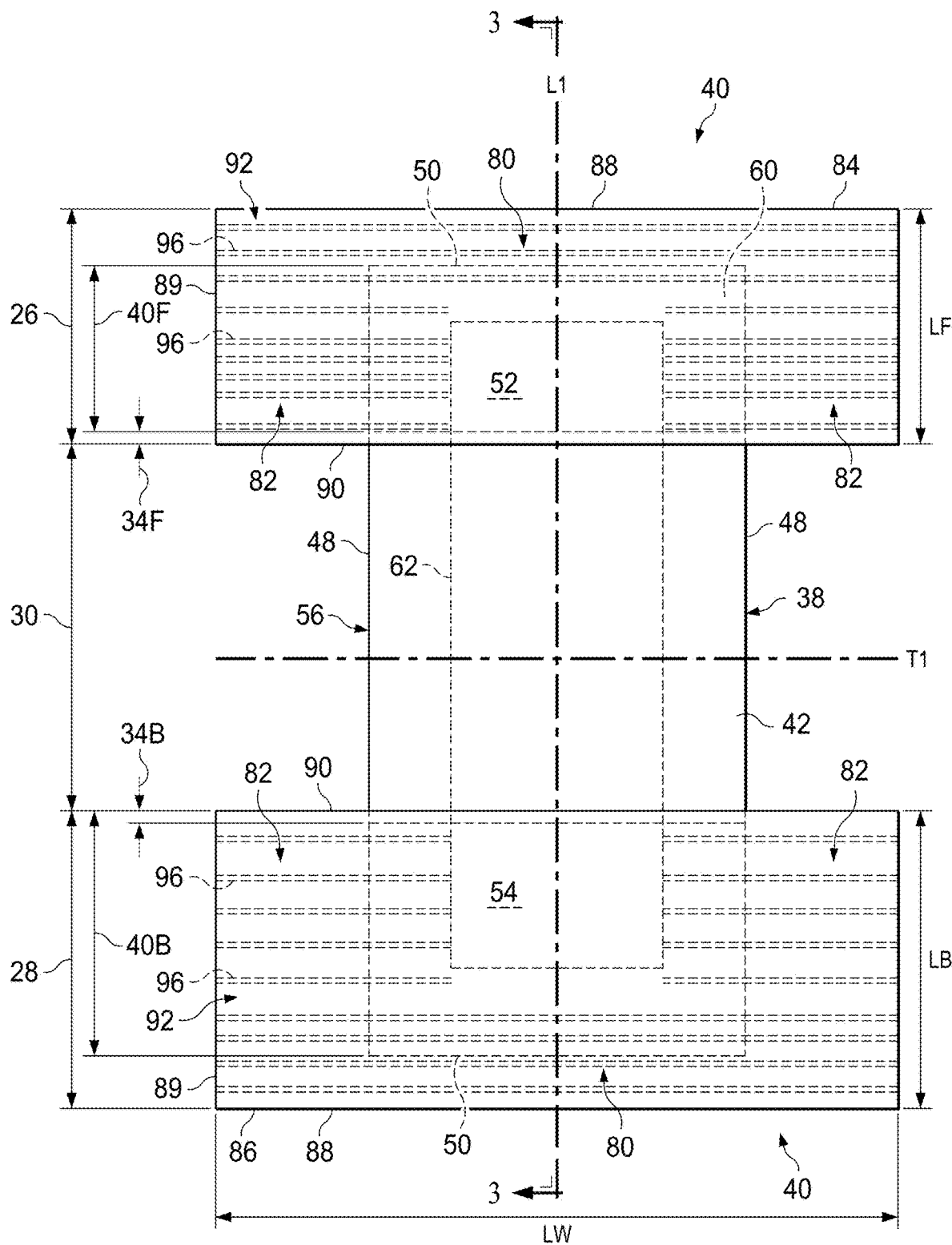
FIG. 2 is a schematic plan view of one embodiment of a wearable article of the present disclosure with the seams unjoined and removed, and in a flat uncontracted condition showing the garment facing surface.

FIG. 1 is a perspective view of an embodiment of the wearable article 20 of the present disclosure. FIG. 2 is a schematic plan view of the wearable article of FIG. 1 with the seams enjoined and in its flat uncontracted condition showing the garment-facing surface. Referring to FIGS. 1 and 2, the wearable article 20 has a longitudinal centerline L1 which also serves as the longitudinal axis, and a transverse centerline T1 which also serves as the transverse axis. The wearable article 20 of the present disclosure has a skin-facing surface, a garment-facing surface, a front region 26, a back region 28, a crotch region 30 between the front region 26 and the back region 28, and seams 32 which join the front region 26 and the back region 28 in their the transverse edges to form two leg openings and a waist opening. The wearable article 20 comprises a main body 38 disposed in the crotch region 30, and the front region 26 and back region 28 at least in part in a longitudinal direction so that the front, crotch and back regions are continuous. In the embodiment shown in FIG. 1, the front belt 84 and the back belt 86 define the front region 26 and the back region 28, respectively. The front and back belts 84, 86 may jointly form a ring-like elastic belt 40 (hereinafter may be referred to as "waist belt") extending transversely defining the waist opening. The transverse edges of the front belt 84 and the back belt 86 are joined by seams 32 to form a waist opening, and two leg openings jointly with the main body 38.

Referring to FIG. 2, the main body 38 may contain an absorbent core 62 for absorbing and containing body exudates disposed in the main body 38. The wearable article 20 may also comprise an outer cover layer 42 to cover the main body 38. The front and back belts 84, 86 may overlap at least a portion of the main body 38 and one or both of the belt portions may be disposed in the garment-facing surface of the main body 38 or alternatively on the body-facing surface of the main body. The main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 may be joined to a front waist panel 52 of the main body 38, the center of the back belt 86 is joined to a back waist panel 54 of the main body 38, the front and back belts 84, 86 each having a left side panel and a right side panel 82 where the main body 38 does not overlap. The left side panel and right side panel 82, 86 sandwich the center of the front belt 84 and the center of the back belt 86.

Referring to FIGS. 1 and 2, the belt 40 formed at least partly by the front belt 84 and back belt 86 acts to dynamically create fitment forces and to distribute the forces dynamically generated during wear. Herein, the term "proximal" is used to indicate the position of a "proximal" portion being closer relative to the transverse centerline T1 of the article. Therefore, the proximal edge 90 of the belt 40 is located closer than the distal edge 88 of the belt relative to the transverse centerline T1. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. For example, the front leg opening region 120 is disposed adjacent the leg opening along the proximal edge 90 of the left and right side panels 82 of the front belt 84.

The front and back belts 84, 86 may be continuous or discontinuous with one another in the crotch region 30. When the front and back belts 84, 86 are discontinuous, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

The front belt 84 and back belt 86 may each comprise an inner sheet 94, an outer sheet 92, (hereinafter also collectively "belt sheets") and configured to impart elasticity to the belt 40. Each of the front and back belts 84, 86 may be made of a single elastic panel, a plurality of elastic panels, or as a laminate having a plurality of elastic strands 96 sandwiched between the inner and outer sheets 94, 92 to impart elasticity in the front and back regions 26, 28. In one embodiment, the elastic strands 96 extend in a transverse direction to provide a ring like elastic belt 40 when the front belt 84 and the back belt 86 are joined. At least some of the elastic strands 96 extend in the transverse direction substantially parallel to each other. All of the elastic strands 96 may extend in the transverse direction substantially parallel to each other. Such an article may be economically made.

While not depicted in the Figures, the front and back belt 84, 86 may be made of an elastic substrate, or by less than or more than 2 layers. Further, the front belt 84 and the back belt 86 may be made of different materials and/or layers. When the front belt 84 and the back belt 86 are made of the same inner sheet 94, the same outer sheet 92 and plurality of elastic strands 96 respectively, the elastic strands 96 may be disposed in the same or different denier, interval, and force between the front and back, as well as in different longitudinal positions of the belt. The front and/or back belt 84, 86 may be treated such that certain of the area overlapping the front and/or back waist panel of the main body 38 are removed of elasticity. Removal of elasticity from the area where an artwork is displayed may help the visibility of the artwork.

The effective transversal width LW of the back belt 86 in the uncontracted condition may be the same as the transversal width of the front belt 84 of the same condition. By "effective transversal width", what is meant is the width available for forming the wearer-facing surface of the article. Each of the proximal edges 90 and the distal edges 88 of the front belt 84 and the back belt 86 may be substantially parallel, as in FIG. 2.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90. In such embodiment, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Whether or not the longitudinal length LB of the back belt 86 and the longitudinal length LF of the front belt 84 are the same, the entirety of the longitudinal length LF of the belt side edge 89 of the front belt 84 is seamed with the belt side edge 89 of the back belt 86 to define a seam length LS. When the front belt 84 has straight distal edges 88 and proximal edges 90 that are substantially parallel of each other, then the longitudinal length LF of the front belt 84 is equal to the seam length LS.

The outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. The front and back belts 84, 86 may be provided in low caliper non-woven material for sake of breathability and softness of the belt 40.

Referring to FIGS. 2 and 3, the main body 38 comprises an outer cover layer 42 and a backsheet 60 attached to the skin-facing surface of the outer cover layer 42. The outer cover layer 42 may be disposed in the garment-facing surface 22 of the wearable article 20 to cover at least the crotch panel 56 of the main body 38 in a longitudinal direction. The outer cover layer 42 extends into and covers part of one or both of the front waist panel 52 and the back waist panel 54 of the main body 38. The outer cover layer 42 may form a portion of the backsheet and/or the main body. The outer cover layer 42 may be directly joined to and cover a portion of the liquid impervious backsheet 60 of the main body 38. The central panel 80 of the front and back belts 84, 86 may be joined to the front and back waist panels 52, 54 of the main body 38 through the outer cover layer 42 so that the outer cover layer 42 is disposed between the front and back belt 84, 86, and the liquid impervious backsheet 60 of the main body 38. The outer cover layer 42 extends only partly in the longitudinal direction of the front waist panel 52 and/or the back waist panel 54 to leave the distal parts of the front waist panel 52 and/or the back waist panel 54 free of the outer cover layer 42. Namely, the longitudinal length of the outer cover layer 42 may be longer than the longitudinal length of the crotch panel 56 and is shorter than the longitudinal length of the backsheet 60. By such configuration, the distal parts of the front waist panel 52 and/or the back waist panel 54 are devoid of the outer cover layer 42, providing better breathability as the overall article. Further, such configuration may provide cost saving compared to the configuration of FIG. 4. Accordingly, looking at the layers of elements between the garment-facing surface and the backsheet 60 of the main body 38, there may be 5 regions from the front distal side to the back distal side; 1) a front waist graphic region 40F disposed on the front waist panel 52 where the outer cover layer 42 is absent; 2) a front transitional region 34F disposed on the front waist panel 52 where the outer cover layer 42 exists; 3) a crotch graphic region disposed on the crotch panel 56; 4) a back transitional region 34B disposed on the back waist panel 54 where the outer cover layer 42 exists; and 5) a back waist graphic region 40B disposed on the back waist panel 54 where the outer cover layer 42 is absent. Looking at the layers of elements between the garment-facing surface and the backsheet 60 of the main body 38, the crotch graphic region is made of only the outer cover layer 42 and the waist graphic regions 40F, 40B are made of the layers for making the elastic belt 40, while the transitional regions 34F, 34B are made of both the outer cover layer 42 and layers making the elastic belt 40.

For providing attractive printing for a wearable article in an economical manner, it is common practice to provide printing on the garment-facing side of the backsheet 60. The longitudinal length of the front waist graphic region 40F or back waist graphic region 40B may be made as long as possible. The longitudinal length of the front waist graphic region 40F may be more than about 50%, or more than 60%, or more than 70%, or more than 80% of the longitudinal length of the front waist panel 52. The longitudinal length of the back waist graphic region 40B may be more than about 50%, or more than 60%, or more than 70%, or more than 80% of the longitudinal length of the back waist panel 54. The longitudinal length of the transitional region 34F, 34B may be made as short as possible.

The longitudinal length of the transitional region 34F, 34B may be less than 20 mm, or less than 15 mm, or less than 10 mm. By providing the transitional region 34F, 34B as small as possible, more attractive printing can be provide in an economical manner. By avoiding displaying a graphic in the transitional region 34F, 34B, especially in the front transition region 34F, the compromised appearance between the graphic in the waist graphic region and the graphic in the transitional region may be avoided.

The main body 38 may further comprise a liquid pervious topsheet 58 and an absorbent core 62 for absorbing and containing body exudates disposed between the topsheet 58 and the backsheet 60. The topsheet 58 may be positioned adjacent the body-facing surface of the absorbent core 62 and may be joined thereto and/or to the backsheet 60 by any attachment means known in the art. The topsheet 58 may be positioned adjacent the body-facing surface of the absorbent core 62 and may be joined thereto and/or to the backsheet 60 by any attachment means known in the art. The liquid impervious backsheet 60 is generally that portion of the wearable article 20 positioned adjacent the garment-facing surface of the absorbent core 62 and prevents the exudates absorbed and contained therein from soiling articles that may contact the wearable article 20.

The topsheet 58, the backsheet 60 and the absorbent core 62 suitable for the wearable article according to the present disclosure may be manufactured from many known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet and may be formed from films, microporous and/or monolithic films, woven and nonwoven webs and the like as well as combinations of these materials. The woven or nonwoven webs of the backsheet may be formed of natural fibers (e.g., wood or cotton fibers), synthetic fibers (e.g., polyester or polypropylene fibers), or a combination of natural and synthetic fibers.

A suitable absorbent core for use in the wearable article 20 may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some embodiments, the absorbent core may comprise one or more elements including a fluid acquisition component, a fluid distribution component, and a fluid storage component. Examples of a suitable absorbent core having a fluid acquisition component, a fluid distribution component, and a fluid storage component are described in U.S. Pat. Nos. 6,590,136, 6,664,439 and 6,989,006.

The first and second belt 84, 86 may comprise any known materials. Suitable material for the first and second belt 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. The belt may comprise a nonwoven web of synthetic fibers. The belt may comprise a stretchable or elastomeric nonwoven, elastomeric film, strands, ribbons or the like and combinations thereof. The belt may comprise an inner hydrophobic, non-stretchable nonwoven material and an outer hydrophobic, non-stretchable nonwoven material.

The outer and inner sheets 92, 94 may be formed of substantially the same material or may comprise different materials. The outer and inner sheets 92, 94 may be formed from nonwovens, films, foams, elastic nonwoven, or combinations thereof.

The elastic strands 96 may comprise one or more elastic strands, elastomeric films, elastomeric ribbons, elastomeric nonwovens, elastomeric filaments, elastomeric adhesives, elastomeric foams, scrims or combinations thereof. In certain embodiments, one or both of the outer and inner sheets 92, 94 may be formed from an elastomeric material as described above.

The topsheet 58, the backsheet 60 and the absorbent core 62 suitable for the wearable article according to the present disclosure may be manufactured from many known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet and may be formed from films, microporous and/or monolithic films, woven and nonwoven webs and the like as well as combinations of these materials. The woven or nonwoven webs of the backsheet may be formed of natural fibers (e.g., wood or cotton fibers), synthetic fibers (e.g., polyester or polypropylene fibers), or a combination of natural and synthetic fibers.

A suitable absorbent core for use in the wearable article 20 may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some embodiments, the absorbent core may comprise one or more elements including a fluid acquisition component, a fluid distribution component, and a fluid storage component. Examples of a suitable absorbent core having a fluid acquisition component, a fluid distribution component, and a fluid storage component are described in U.S. Pat. Nos. 6,590,136, 6,664,439 and 6,989,006.

The leg elastic material 140 may be disposed so as to extend generally longitudinally along the longitudinal side edge 48 of the main body 38. The leg elastic material 140 may be disposed at least in the crotch region 30 of the wearable article 20 or may be disposed along the entirety of the longitudinal side edge 48.

The outer cover layer 42 may comprise a material separate from the material of the inner sheet 94 and/or the outer sheet 92 constituting the belt 40. The outer cover layer 42 may comprise two or more layers of materials. The outer cover layer 42 may comprise any known materials and may comprise materials used for the first and second belt 84, 86 as explained above. The outer cover layer 42 may comprise a single layer of nonwoven web of synthetic fibers, natural fibers or combinations of natural and synthetic fibers. The outer cover layer 42 may comprise a film, a foam, a nonwoven, a woven material or the like and/or combinations thereof such as a laminate of a film and a nonwoven.

The first and second belt 84, 86 may comprise any known materials. Suitable material for the first and second belt 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. The belt may comprise a nonwoven web of synthetic fibers. The belt may comprise a stretchable or elastomeric nonwoven, elastomeric film, strands, ribbons or the like and combinations thereof. The belt may comprise an inner hydrophobic, non-stretchable nonwoven material and an outer hydrophobic, non-stretchable nonwoven material.

The outer and inner sheets 92, 94 may be formed of substantially the same material or may comprise different materials. The outer and inner sheets 92, 94 may be formed from nonwovens, films, foams, elastic nonwoven, or combinations thereof.

The elastic strands 96 may comprise one or more elastic strands, elastomeric films, elastomeric ribbons, elastomeric nonwovens, elastomeric filaments, elastomeric adhesives, elastomeric foams, scrims or combinations thereof. In certain embodiments, one or both of the outer and inner sheets 92, 94 may be formed from an elastomeric material as described above.

Graphic Regions

Referring to FIGS. 2 and 3, the wearable article of the present disclosure comprises a front waist graphic region 40F and a back waist graphic region 40B. The front waist graphic region 40F is disposed on a front waist panel 52 where an outer cover layer 42 is absent, and a back waist graphic region 40B is disposed on a back waist panel 54 where the outer cover layer is 42 absent. At least one of the front waist graphic region 40F and the back waist graphic region 40B comprises a waist graphic printed on a main body 32.

The wearable article of the present disclosure further comprises a first belt graphic disposed on one or both of the front and back belts. The first belt graphic is not provided by the main body.

The first belt graphic may be single graphic or a cluster of multiple graphic units. When the first belt graphic is a cluster of multiple first graphic units, the first graphic units can be provided in regular or random arrangement in a wearable absorbent. Some of the first graphic units may have color different from other graphic units.

In some embodiments, the first belt graphic is disposed along at least part of the waist circumference of the wearable article. For example, the first belt graphic is disposed at or adjacent to the waist opening, and extends circumferentially about the waist opening. In other embodiments, the first belt graphic is disposed at an area adjacent to at least part of each of leg openings of the wearable article. "Adjacent" to the waist opening or the leg opening means that the distance between the waist opening or leg opening is less than about 15 mm, or about 10 mm, or about 5 mm. In other embodiments the first belt graphic is disposed at an area adjacent to the seam 32. In other embodiments, the first belt graphic is disposed in an area overlapping with at least one of the front waist panel 52 and the back waist panel 54.

The first belt graphic may be continuous or non-continuous. The first belt graphic may be a linear or wavy pattern in a longitudinal direction. The term "linear pattern" is intended to mean a pattern parallel with a waist edge (waist periphery) as a whole, and the linear pattern does not always need to be straight linear. For example, a linear pattern may be a composite of two or more non-straight linear segments such as curved line segments arranged substantially parallel with a waist edge as a whole. The linear pattern does not always need to be parallel with the waist edge in every microscopic detail in the plan view, and can be a pattern extending along the waist edge when seen macroscopically. To provide a better underwear-like look to the article, when the first belt graphic is a linear or wavy pattern, it may have a width in a transversal direction at least about 10 mm or at least about 15 mm. The first belt graphic may be continuous from a one side seam to the opposing side seam. The first belt graphic may be single graphic or a cluster of multiple graphic. The multiple colored graphic can be provided in regular or random arrangement in a wearable absorbent.

The wearable article of the present disclosure may further comprise a second graphic region disposed on one or both of the front and back belts. The second graphic region comprises a second belt graphic. The second belt graphic may be created by a second colored material which differs from the first colored material. Materials different from only in color are not considered a different material in the present disclosure context. Descriptions stated with respect to the first belt graphic above are applicable for the second colored graphic.

The first belt graphic and the second graphic may be the same pattern or different patterns. The first belt graphic and the second belt graphic may be spaced apart each other, or overlap with each other at least in part.

The combinations of the various artworks described herein, may be coordinated to create a uniform graphical element, such as common colors, shapes and/or patterns, and/or associated shapes, etc.

Any material applicable to a component consisting of wearable articles and providing colored graphics can be used to create the first belt graphic. The material for the first belt graphic may be in a liquid form when applied to a component consisting of wearable articles and become solid after applied to, such as adhesive and printing ink. The material for the first belt graphic may be in a solid form when applied, a component consisting of wearable articles and remains a solid once it is applied, such as elastic strands, fibers and web.

The material for the first belt graphic may be selected from the group consisting elastic strands, adhesive, printing ink, web and combinations thereof. Use of one of components consisting of the front and back regions 26, 28 as a material to create the belt graphic may be preferable in the cost effectiveness point of view.

The material for the first belt graphic may be a colored elastic strand. Each of the front and back regions 26, 28 comprises an outer sheet 92, an inner sheet 94, and a plurality of elastic strands 96 sandwiched between the outer and inner sheets 92, 94. When the material for the first belt graphic is a colored elastic strand, one or more elastic strands of the plurality of elastic strands 96 are colored elastic strands. Elastic strands 96 can be provided to the front and back regions 26, 28 by various methods and apparatus well known to those skilled in art. For example, elastic strands 96 is provided in the belt 40 by advancing the outer and inner sheets 92, 94 and a plurality of elastic strands 96 in the machine direction, stretching the elastic strands 96 in the machine direction, and adhering certain portions of the three components one another. The adhesion may be provided by holt-melt adhesive method, heat bonding, ultrasonic bonding, or any other method known in the art. The elastic strands in the elastic region are not cut. By such steps and after the tension stretching the elastic strands are eventually removed, the elastic strands return to their relaxed state to create gathers with the outer and inner sheets 92 and 94 as shown in FIG. 1. The elastic strands 96 including colored elastic strands may be positioned in any interval between each other, in any length in a longitudinal direction to meet needs.

The material for the first belt graphic may be adhesive. The front and back regions 26, 28 comprises an outer sheet 92, an inner sheet 94, a plurality of elastic strands 96 sandwiched between the outer and inner sheets 92, 94, and the outer and inner sheets and/or the elastic strands can be adhered with each other by adhesive. The adhesive may be in the form of meltblown adhesive, spray coating resins, or web forming resins, and disposed in the inner side of either the outer or inner sheet. For example, hot melt adhesives are applied to an advancing web in pre-determined pattern by slot die coating, direct gravure, offset gravure and reverse gravure roll coating processes that are extensively described in the art. Adhesive may be applied in various patterns on an inner side of the outer and/or inner sheets to bond the sheets. A shape of a pattern, a width and length of each pattern or an interval between two adjacent patterns can be determined to meet needs. When the material for the first belt graphic is adhesive, one or more adhesive patterns are provided to provided belt graphic. For example, adhesive in a pattern may be applied using slot die coating employing a slot die applicator and a substrate carrier comprising a pattern element disclosed in references such as US 2011/0274834A and US2014/0148773A. It is to be appreciated that the pattern element may be configured in various different shapes and sizes and may be configured to define various different patterns. As such, adhesive may be transferred from the slot die applicator to define various patterns on a substrate, the outer and/or inner sheets 92, 94 in this case.

The material for the first belt graphic may be printing inks. The first belt graphic can be created by printing a graphic on one side, preferable an inner side, of the outer or inner sheet 92, 94 of the belt 40. Graphics on the outer or inner sheet 92, 94 can be printed by various methods and apparatus well known to those skilled in the art such as lithographic, screen printing, flexographic, gravure ink jet printing techniques or a method, and virtually any graphic in any color or color combination can be rendered on the sheet.

Referring to FIGS. 2 and 3, in the third present disclosure, the front belt 84 and the back belt 86 each comprise an inner sheet 94 and an outer sheet 92 wherein a first belt graphic is printed on a garment-facing surface of the inner sheet 94 or a body-facing surface of the outer sheet 92, and a waist graphic is printed on the backsheet 60. By printing graphics in these specific layers, difference of the number of layers, or difference of opacities of layers between the garment-facing surface and the printing is made minimized, thus the appearance difference may be alleviated, and graphics in different regions can provide visual integrity.

The material for the first belt graphic may be a colored web. The colored web may be disposed between the outer and inner sheets 92, 94.

The wearable article may further comprise a second belt graphic disposed on one or both of the front and back belts. The second belt graphic is not provided by the main body. The second belt graphic can be disposed at or adjacent to the seam, or is disposed at or adjacent to at least part of the periphery of each of the leg openings. Descriptions stated with respect to the material for the first belt graphic are applicable for materials for the second belt graphic.

In some embodiments, the first or second belt graphic is provided on a garment-facing surface of the inner sheet 94 or a body-facing surface of the outer sheet 92, and a waist graphic is printed on the backsheet 60 so that the intensity of the belt graphic and the waist graphic appear to be more substantially similar when observed as an article from the garment-facing side.

The wearable article may further comprise a crotch graphic region disposed on the crotch panel 56 comprising a crotch graphic. In one embodiment, when the wearable article comprises a waist graphic in one of the waist panels 52, 54 and a crotch graphic in the crotch graphic region 30, the waist graphic and the crotch graphic may form a continuous graphic.

Figure 5:
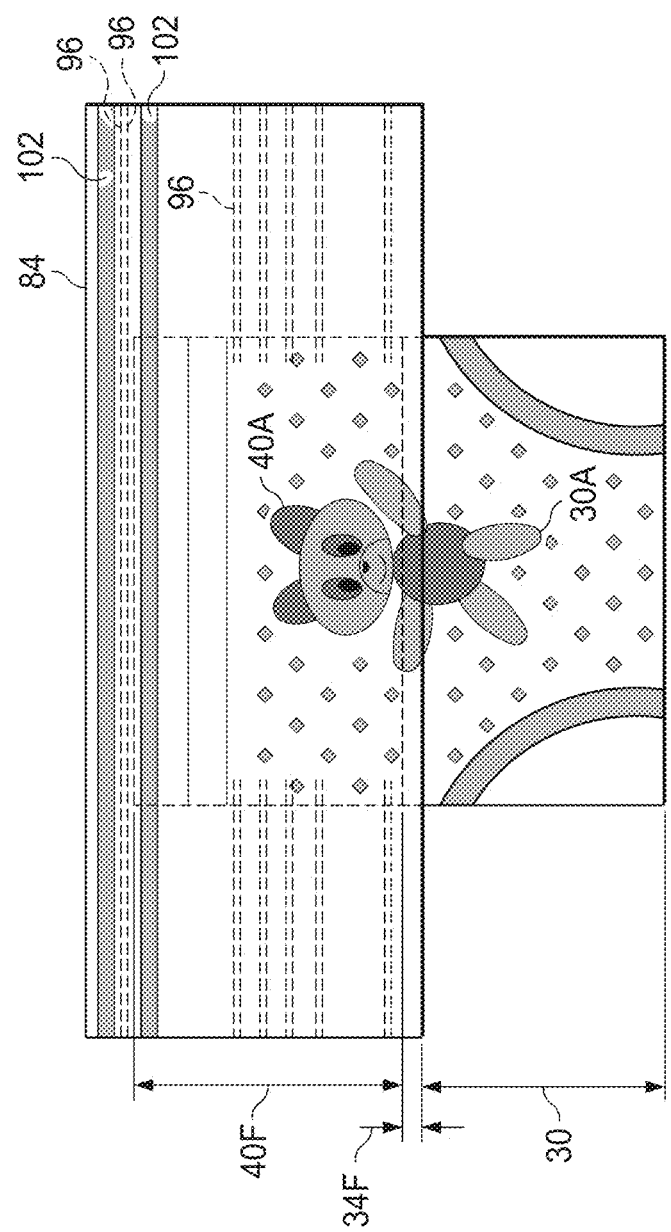
FIG. 5 is a partial schematic plan view of one embodiment of a wearable article of the present disclosure showing the garment facing surface.

Referring to FIG. 5, in some embodiments, a wearable article comprises a first belt graphic 102 which is a print disposed on an inner side of the outer sheet 92 or the inner sheet 94, and the front and/or back graphic region 34F comprising a waist graphic 40A. The first belt graphic 102 is disposed at or adjacent a waist edge and extends circumferentially about the waist edge the front belt 84. The waist graphic 40A is printed in the main body, for example on the backsheet. When the opacity of the outer sheet 92 is OO and the opacity of one or both of the front belt and the back belt comprising the waist graphic is OB, the difference between OO and OB is less than 20%, or less than about 15%, or less than about 10%. The opacity of a sheet material is measured according to the "Measurement of Opacity" described below. By providing OO and OB to have less than 20% difference, the appearance of the first belt graphic and the waist graphic may be made less different for example in view of intensity to the observer, and therefore provide a better visual integrity. The value of OO may be from about 15% to about 70%, or from about 20% to about 50%. The value of OB may be from about 15% to about 85%, or from about 20% to about 70%. The values OO and OB may be adjusted by selecting materials for making the outer and inner sheets 92, 94 as explained in detail below as well as according to any manner known in the art.

The wearable article may further comprise crotch graphic region 30 comprise a crotch graphic 30A. The waist graphic 40A and the crotch graphic 30A are printed on the backsheet, wherein when the opacity of the outer cover layer is OC and the opacity of one or both of the front belt and the back belt comprising the waist graphic is OB, the difference between OC and OB is less than 20%. By providing OB and OC to have less than 20% difference, the appearance of the waist graphic and the crotch graphic may be made less different to the observer, and therefore provide a better visual integrity. The difference between OC and OB may be less than about 20%, or less than about 15%, or less than about 10%. The value of OC may be from about 15% to about 70%, or from about 20% to about 50%. The value of OB may be from about 15% to about 85%, or from about 20% to about 70%. The values OC and OB may be adjusted by selecting materials for making the belt sheets 92, 94 and the outer cover layer 42, as explained in detail below. All of the waist graphic and the crotch graphic may be printed on the backsheet.

Examples of materials suitable for the outer sheet 92 and inner sheet 94 include nonwoven material of 5-50 g/m$^2$. Nonwoven polyolefins such as polypropylene may be suitable for use. Examples of materials suitable for the outer cover layer 42 include nonwoven material of 5-50 g/m$^2$. Patterned, quilted, or embossed material may be useful for connoting softness or high quality of the article.

The outer cover layer 42 may be provided opaque by adding a white-tinting/opacifying agent to the polymer resin that is spun to make the nonwoven material. While a variety of whitening/opacifying agents may suffice, it is believed that titanium dioxide ($TiO_2$) may be particularly effective because of its brightness and relatively high refractive index. It is believed that addition of $TiO_2$ to the polymer(s) from which the fibers are to be formed, typically in an amount up to 5.0% by weight of the nonwoven, may be effective to achieve the desired results. It is believed that the increased opacity provided by whitening/opacifying agents helps to produce a visually distinctive, soft appearance of the nonwoven. It also may be desired in some applications that a coloring or tinting agent be added to one or more the polymer resin(s) from which the nonwoven fibers will be spun.

Opacity can also be enhanced by using fiber having cross-sectional shapes other than round and solid (non-hollow) geometries, namely trilobal or multilobal cross-sections, or hollow configurations or combinations thereof. Those non-circular cross-sectional shapes can also provide advantages in terms of loft and compression resilience.

Figure 6:
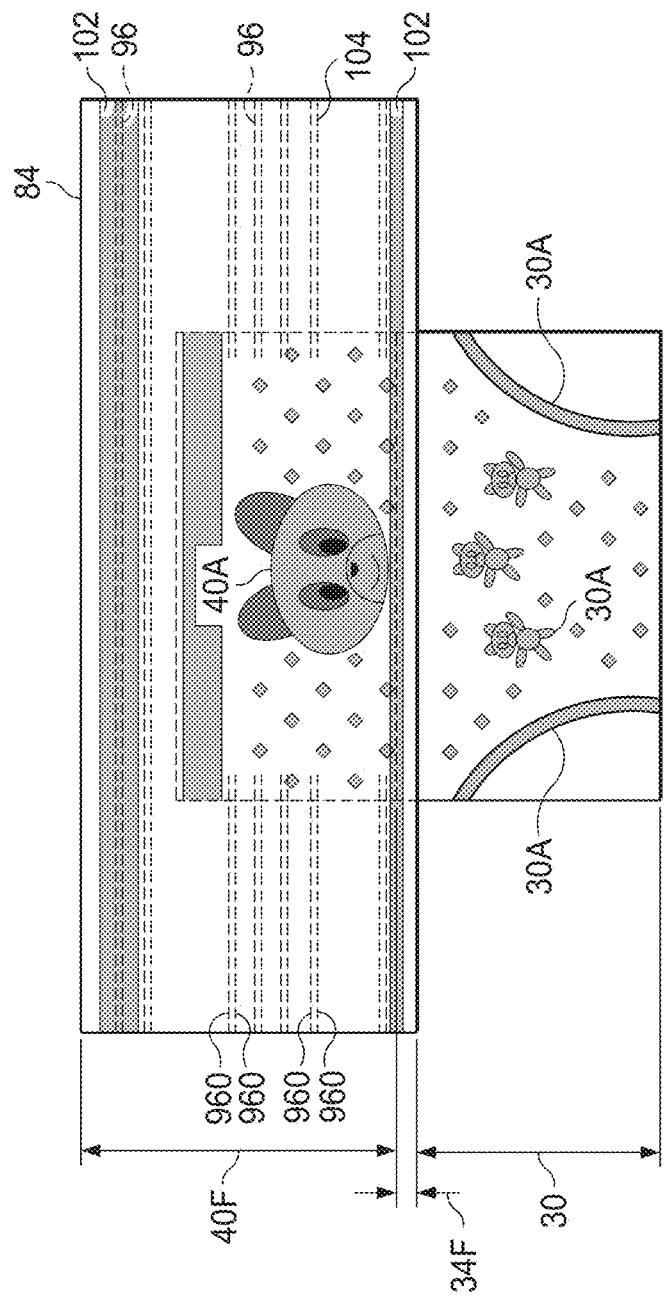
FIG. 6 is a partial schematic plan view of another embodiment of a wearable article of the present disclosure showing the garment facing surface.

Referring to FIG. 6, in other embodiments, a wearable article comprises a first belt graphic 102 provided by adhesive, a second belt graphic 104 provided by colored elastic strands, and the front waist region 40F and/or back waist graphic region 40B comprising a waist graphic 40A printed on the back sheet 60. The first belt graphic 102 is disposed at or adjacent a waist edge and extends circumferentially about the waist edge the front belt 84. The article may further comprise a crotch graphic 30A in a crotch region 30 such that the first graphic 102 or the second graphic 104 disposed at or adjacent the proximal edge 90 and the crotch graphic 30A are aligned to create a composite graphical element that may or may not be uniform around a leg opening. The transitional region 34F has no graphic, so that the compromised appearance between the graphic in the waist graphic region and the graphic in the transitional region is avoided.

In FIGS. 5-6, the back belt which is not shown in the drawings may have the same first belt graphic and/or the waist graphic as those disposed in the front belt 84, or may have different graphics.

Measurement of Opacity

The opacity of a material, or materials combined, is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab LabScan XE running Universal Software (available from Hunter Associates Laboratory Inc., Reston, Va., US). Instrument calibration and measurements are made using the standard white and black calibration plates provided by the vendor. All testing is performed in a room maintained at about 23±2° C. and about 50±5% relative humidity.

The spectrophotometer is configured for the XYZ color scale, D65 illuminant, 10° standard observer, with UV filter set to nominal. The instrument is standardized according to the manufacturer's procedures using the 44.45 mm (1.750 inch) area view. After calibration, the software is set to the Y opacity procedure which prompts the operator to cover the sample with either the white or black calibration tile during the measurement.

To obtain a specimen, lay the sample flat on a bench, body facing surface downward, and 101.6 mm by 101.6 mm portions of sample are cut using scissor for analysis. When the sample is a combined material, they are overlayed to obtain a specimen. Samples are pre-conditioned at 23° C.±2 C.° and 50%±5% relative humidity for two hours prior to testing.

Place specimen over the measurement port. The specimen should completely cover the port with the surface corresponding to the garment-facing surface of the article directed toward the port. Cover the specimen with the white standard plate. Take a reading, then remove the white tile and replace it with the black standard tile without moving the specimen. Obtain a second reading, and calculate the opacity as follows:

$$\text{Opacity} = (Y \text{value}_{(black\ backing)} / Y \text{value}_{(white\ backing)}) \times 100$$

A total of three identical material, or materials combined, are analyzed and their opacity results recorded. Calculate and report the average opacity to the nearest 0.1%.

Measurement of Color

The color of graphics can be measured using the CIE L*a*b* color system (CIELAB). The L*, a*, and b* values are measured from the garment-facing surface 22 of the wearable article 20. As an example, a flat bed scanner capable of scanning a minimum of 24 bit color at 1200 dpi and has manual control of color management such as an Epson Perfection V750 Pro (Epson America Inc., Long Beach Calif., US) or any scanner having equivalent functions is used to acquire images. The scanner is calibrated against a color reflection target compliant to ANSI method IT8.7/2-1993 using color management software such as MonacoEZColor available from X-Rite Grand Rapids, Mich. or any software having equivalent functions to construct a scanner profile. The resulting calibrated scanner profile is opened within an imaging program that supports sampling in CIE L*a*b* such as Photoshop S4 available from Adobe Systems Inc., San Jose, Calif., US or any imaging program having equivalent functions to measure colored graphics.

Turn on the scanner for 30 minutes prior to calibration. Place the IT8 target face down onto the scanner glass and close the scanner lid. Open the MonacoEZColor software and select acquire image using the Twain software included with the scanner. Within the Twain software deselect the unsharp mask setting and any automatic color correction or color management options that may be included in the software. If the automatic color management cannot be disabled, the scanner is not appropriate for this application. Acquire a preview scan at 200 dpi and 24 bit color. Insure that the scanned image is straight and first garment-facing surface facing side-up. Crop the image to the edge of the target, excluding all white space around the target, and acquire the final image. The MonacoEZColor software uses this image to compare with included reference files to create and export a calibrated color profile compatible with Photoshop. After the profile is created the scan resolution (dpi) can be changed, but all other settings must be kept constant while imaging samples.

Identify an area in the garment-facing surface 22 where the graphic of interest is perceived. For convenience of handing, the sample size may be a 75 mm by 75 mm piece, however, as will be appreciated by the person skilled in the art, smaller samples sizes can be used. Keep all layers in the sample intact and place all layers on the scanner flat etc. Open the scanner lid and place the sample onto the scanner glass with the first garment-facing surface facing the glass. Cover the sample with the white background (in this test method white is defined as having L*>94, −2<a*<2, and −2<b*<2) and close the lid. Acquire and import a scan of the sample into Photoshop at 600 dpi and 24 bit color. Assign the calibrated scanner profile to the image and change the mode to Lab Color ("Lab Color" in Photoshop corresponds to the CIE L*a*b* standard). Select the "eyedropper" color selection tool. Set the sampling size of the tool to include as many pixels as possible within a colored graphic without including pixels from adjacent non-colored areas. Using the eyedropper tool, measure and record L*a* b* values in the graphic in the image.

EXAMPLES

Inventive Samples A-E according to the present disclosure have the structure of the belt-type wearable article of FIGS. 2 and 3 in which the longitudinal length of the front waist graphic region is 100 mm and the longitudinal length of the front transitional region is 10 mm. Comparative Sample E has the structure of the belt-type wearable article of FIGS. 2 and 3 in which the longitudinal length of the front waist graphic region is 100 mm and the longitudinal length of the transitional region is 10 mm, and has an opacity difference between OB and OO of more than about 20%. Comparative Samples F-I have the structure of the belt-type wearable article of FIG. 4 without front and back waist graphic regions.

All samples are provided with the same belt graphic disposed adjacent to the waist edge, waist graphic 40A disposed on the waist graphic region, and the crotch graphic 30A disposed on the crotch region, both of which were printed on the same position of the backsheet 60.

All materials for the outer cover layer 42, inner sheet 94 and outer sheet 92 in the samples have the same compositions, but have difference in basis weight (g/m$^2$). The visual integrity of the holistic graphic was observed by a trained expert panel and evaluated. The results are shown below.

TABLE

| Sample | Belt Outer sheet (g/m$^2$) | OO (%) | Belt Outer/Inner sheets (g/m$^2$) | OB (%) | OB − OO (%) | Outer cover layer (g/m$^2$) | OC (%) | OB − OC (%) | Opacity of transitional region (%) | Visual integrity*[1] | Visual integrity*[2] |
|---|---|---|---|---|---|---|---|---|---|---|---|
| A | 17 | 20.1 | 17 + 10 | 37.4 | 17.3 | 17 | 20.1 | 17.3 | 50.0 | Good | Good |
| B | 17 | 20.1 | 17 + 17 | 36.4 | 16.3 | 17 | 20.1 | 16.3 | 49.2 | Good | Good |
| C | 17 | 20.1 | 17 + 10 | 37.4 | 17.3 | 25 | 45.4 | −8.0 | 65.9 | Good | Very Good |
| D | 17 | 20.1 | 17 + 17 | 36.4 | 16.3 | 25 | 45.4 | −9.0 | 65.3 | Good | Very Good |
| E | 25 | 45.4 | 25 + 25 | 70.2 | 24.8 | 25 | 45.4 | 24.8 | 83.7 | Bad | Bad |
| F | 17 | 20.1 | 17 + 10 | 37.4 | 17.3 | 17 | 20.1 | 29.9 | 50.0 | Bad | Bad |
| G | 17 | 20.1 | 17 + 17 | 36.4 | 16.3 | 17 | 20.1 | 29.1 | 49.2 | Bad | Bad |
| H | 17 | 20.1 | 17 + 10 | 37.4 | 17.3 | 25 | 45.4 | 20.5 | 65.9 | Bad | Fair |
| I | 17 | 20.1 | 17 + 17 | 36.4 | 16.3 | 25 | 45.4 | 19.9 | 65.3 | Bad | Fair |

*[1]Visual integrity of the first belt graphic and the waist graphic
*[2]Visual integrity of the waist graphic and the crotch graphic The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article comprising:
   a main body comprising an outer cover layer at a most garment-facing side and a backsheet attached to a body-facing surface of the outer cover layer, wherein the main body has a front waist panel, a back waist panel and a crotch panel between the front waist panel and the back waist panel, and wherein a longitudinal length of the outer cover layer is longer than the longitudinal length of the crotch panel and shorter than a longitudinal length of the backsheet;
   a ring-like belt comprising a front belt and a back belt, wherein each of the front belt and the back belt comprises an inner sheet, an outer sheet and a plurality of elastic strands sandwiched therebetween, wherein the front belt and the back belt are joined by a seam such that a first seam and a second seam are formed so that the article comprises leg openings and a waist opening; and wherein each of the front and back belts has a left side panel and a right side panel where the main body does not overlap, and the center of the front belt is joined to the front waist panel of the main body and the center of the back belt is joined to the back waist panel of the main body;
   a front waist graphic region disposed on the front waist panel where the outer cover layer is absent, and a back waist graphic region disposed on the back waist panel where the outer cover layer is absent, wherein at least one of the front waist graphic region and the back waist graphic region comprises a waist graphic printed on the main body;
   a transitional region disposed on each of the front waist panel and the back waist panel where the outer cover layer exists;
   a first belt graphic disposed on one or both of the front and back belts, the first belt graphic not being provided by the main body; and
   wherein when the opacity of the outer sheet is OO and the opacity of one or both of the front belt and the back belt is OB, and wherein the difference between OO and OB is less than about 20%.

2. The article of claim 1, wherein a longitudinal length of the front waist graphic region is more than about 50% of a longitudinal length of the front waist panel.

3. The article of claim 1, wherein the transitional region disposed on the front waist panel has a longitudinal length less than about 20 mm.

4. The article of claim 1, wherein the belt graphic is provide by a material disposed on a body-facing surface of the outer sheet or a garment-facing surface of the inner sheet.

5. The article of claim 1, wherein the first belt graphic is provided by a material selected from the group consisting of elastic strands, adhesive, printing ink, web, and combinations thereof.

6. The article of claim 1, wherein the first belt graphic is printed on one of the outer sheet and the inner sheet.

7. The article of claim 1, wherein the first belt graphic is disposed at or adjacent to a waist opening periphery and extends circumferentially about the waist opening.

8. The article of claim 1, wherein at least a portion of the first belt graphic is disposed on an area overwrapping with the front waist panel.

9. The article of claim 1, wherein the waist graphic is printed on the backsheet.

10. The article of claim 1, wherein one or both of the front and back belts further comprise a second belt graphic, the second belt graphic not being provided by the main body.

11. The article of claim 10, wherein the second belt graphic is disposed at or adjacent to at least one of the first and second seams.

12. The article of claim 10, wherein the second belt graphic is disposed at or adjacent to at least a portion making up a periphery of each of the leg openings.

13. The article of claim 1, wherein the crotch panel comprises a crotch graphic printed on the backsheet.

14. The article of claim 13, wherein when an opacity of the outer cover layer is OC and the opacity of one or both of the front belt and the back belt comprising the waist graphic is OB, the difference between OC and OB is less than 20%.

15. The article of claim 13, wherein the waist graphic and the crotch graphic form a continuous graphic.

16. The article of claim 1, wherein at least a portion the elastic strands of the front and back belts are cut.

17. The article of claim 1, wherein at least a portion the elastic strands of at least one of the front and back belts overlap at least one of the front waist graphic region and the back waist graphic region.

18. The article of claim 1, wherein at least a portion the elastic strands of at least one of the front and back belts overlap the first belt graphic.

19. The article of claim 1, wherein a longitudinal length of the back belt is longer than a longitudinal length of the front belt.

20. The article of claim 1, wherein the elastic strands of the front and back belts do not overlap an absorbent core of the main body.

* * * * *